United States Patent [19]

Hirshowitz et al.

[11] Patent Number: 5,486,196
[45] Date of Patent: Jan. 23, 1996

[54] APPARATUS FOR THE CLOSURE OF WIDE SKIN DEFECTS BY STRETCHING OF SKIN

[75] Inventors: Bernard Hirshowitz; Amnon Levy; Alexander R. Gilat; Eitan Rogel, all of Haifa, Israel; Jeffrey Stein, Milford, Conn.; Julian Borgia, Belle Mead, N.J.

[73] Assignee: Medchem Products, Inc., Princeton, N.J.

[21] Appl. No.: 55,413

[22] Filed: May 3, 1993

Related U.S. Application Data

[63] Continuation-in-part of Ser. No. 835,636, Feb. 13, 1992, Pat. No. 5,263,971, and a continuation-in-part of Ser. No. 3,751, Dec. 3, 1992.

[51] Int. Cl.[6] .................................................. A61B 17/00
[52] U.S. Cl. ........................ 606/218; 606/150; 606/213; 606/215
[58] Field of Search .................................. 606/212, 213, 606/215–218, 150, 148, 151, 149, 201; 128/20

[56] References Cited

U.S. PATENT DOCUMENTS

| | | |
|---|---|---|
| 268,632 | 12/1882 | Danforth . |
| 376,441 | 1/1888 | Hughes ................................ 606/218 |
| 583,455 | 6/1897 | Bush . |
| 2,450,194 | 9/1948 | Glaser . |
| 3,385,299 | 5/1968 | Le Roy . |
| 3,866,607 | 2/1975 | Forsythe et al. . |
| 3,926,193 | 12/1975 | Hasson . |
| 3,971,384 | 7/1976 | Hasson . |
| 4,506,669 | 3/1985 | Blake, III . |
| 4,512,346 | 4/1985 | Lemole . |
| 4,535,772 | 8/1985 | Sheehan . |
| 4,747,394 | 5/1988 | Watanabe . |
| 4,896,680 | 1/1990 | Hirshowitz . |
| 5,009,663 | 4/1991 | Broome . |
| 5,047,047 | 9/1991 | Yoon . |
| 5,127,412 | 7/1992 | Cosmetto et al. .................... 606/218 |

FOREIGN PATENT DOCUMENTS

| | | |
|---|---|---|
| 0018698 | 11/1980 | European Pat. Off. . |
| 0269935 | 6/1988 | European Pat. Off. . |
| 0279534 | 8/1988 | European Pat. Off. . |

(List continued on next page.)

OTHER PUBLICATIONS

Cohen and Cosmetto, "Suture Tension Adjustment Reel", *J. Dermatol. Surg. Oncol.*, 1992; 18:112–123.

*Primary Examiner*—Stephen C. Pellegrino
*Assistant Examiner*—Jeffrey A. Schmidt
*Attorney, Agent, or Firm*—Robert J. Koch

[57] ABSTRACT

An apparatus for closing wide skin defects may be used with two long interdermal needles configured for insertion underneath skin close to margins of a skin defect. The skin closing apparatus may include two U-shaped retaining members configured as a flange connecting two legs and forming a U-shaped profile. Each of the legs may include a sharp hook at the end of the leg adapted for piercing the skin and engaging one of the long interdermal needles. Each retaining member may include a pivoting platform that pivots up to 20° from an initial position indicated by a detent mechanism. A contracting mechanism such as a screw may connect the retaining members and approximate the interdermal needles, while bringing the skin margins together until final closure of the skin defect results. The skin closing apparatus may also include a clutch mechanism configured to disengage the screw from a knob or handle, when a predetermined force is met or exceeded. A visual or auditory element may also be provided to indicate the amount of force applied to the skin. A retractor may be packaged with the skin closing apparatus and long interdermal needles in a presterilized kit. The retractor may exhibit atraumatic ends having curved edges. The retractor may also exhibit english and metric measuring scales to aid in placing the skin closing apparatus and long interdermal needles about the skin defect. The device may be configured as a single use device utilized with gamma sterilization. In the event the device is configured for multiple uses, any conventional sterilization method may be utilized.

46 Claims, 14 Drawing Sheets

FOREIGN PATENT DOCUMENTS

| | | |
|---|---|---|
| 2289153 | 5/1976 | France . |
| 110664 | 5/1900 | Germany . |
| 2313871 | 10/1973 | Germany .............................. 606/218 |
| 3227984 | 7/1982 | Germany . |
| 3722899 | 1/1989 | Germany . |
| 3834358 | 4/1990 | Germany . |
| 1412751 | 9/1986 | U.S.S.R. . |
| 1560132 | 4/1988 | U.S.S.R. . |
| 1560133 | 7/1988 | U.S.S.R. . |
| 1457906 | 9/1989 | U.S.S.R. . |
| 1556666 | 4/1990 | U.S.S.R. . |

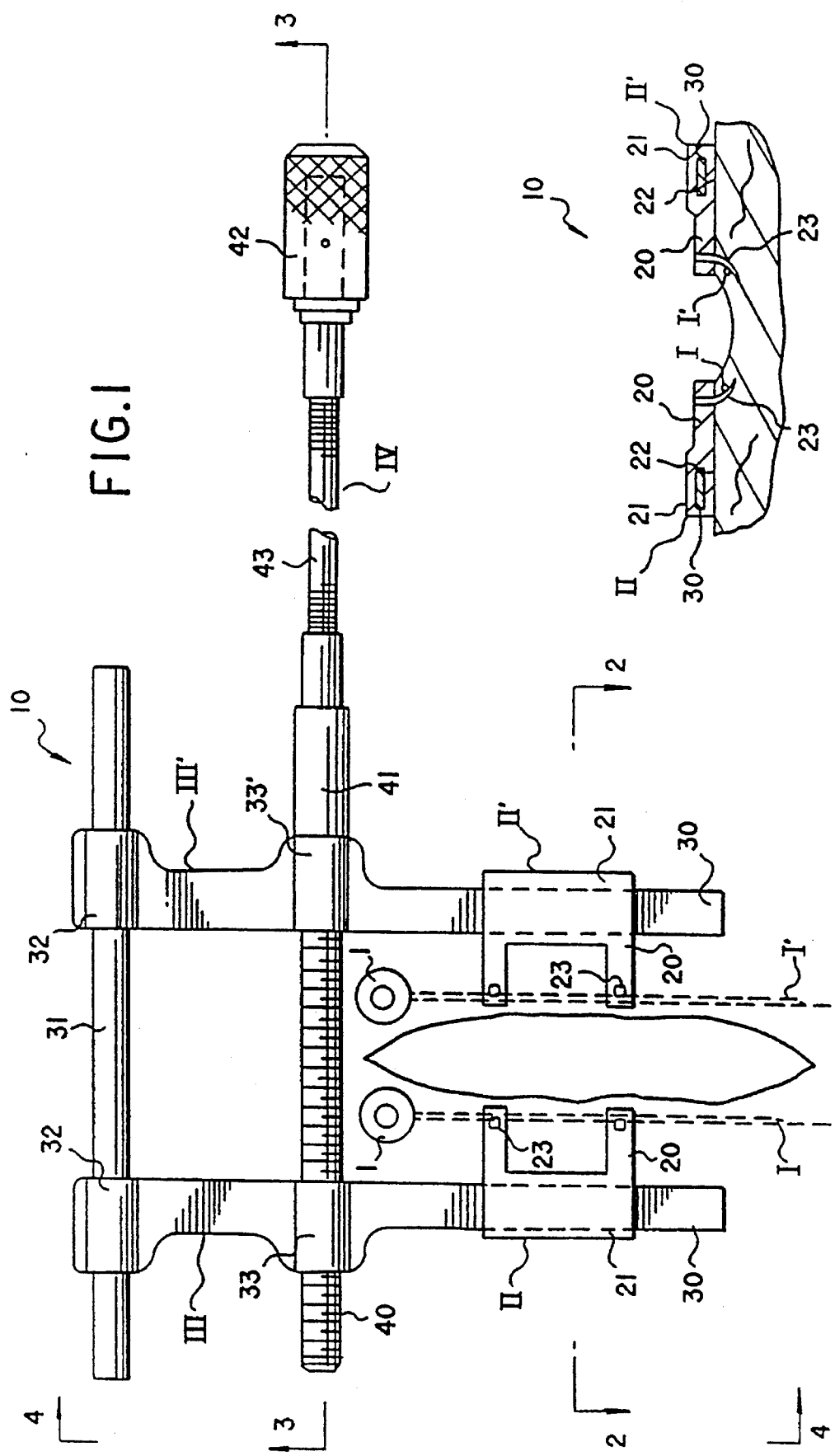

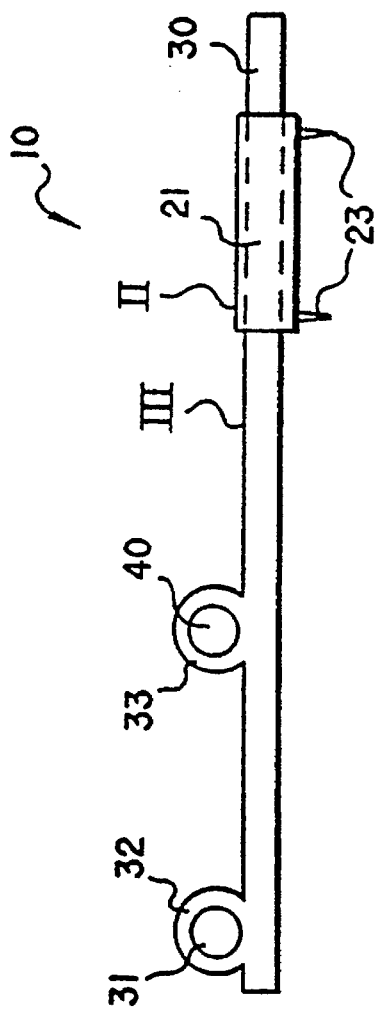
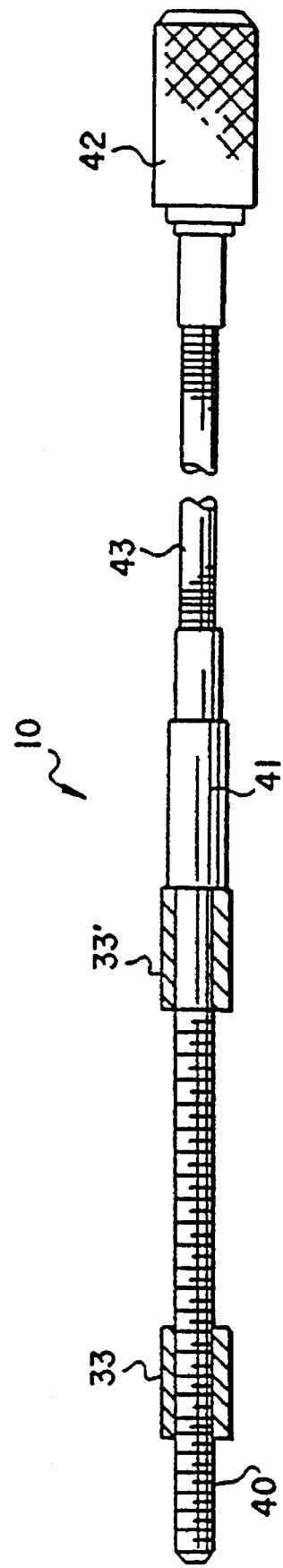
FIG. 4
FIG. 3

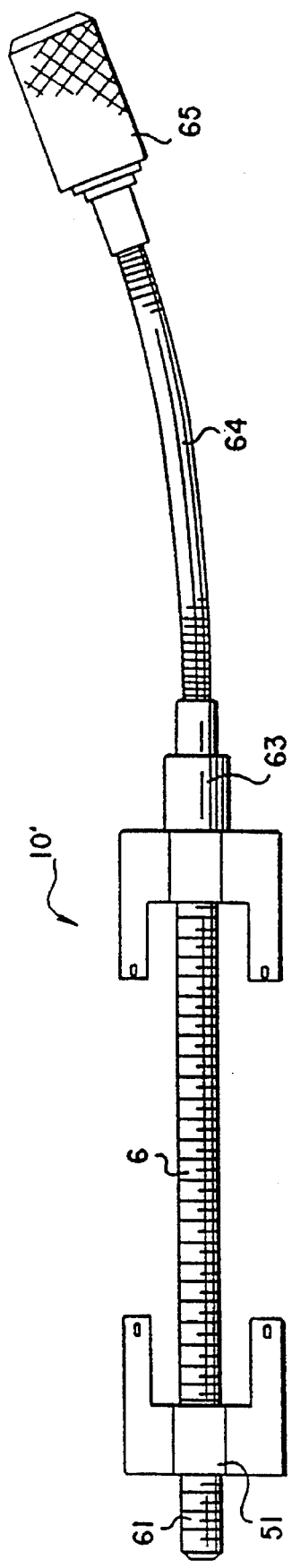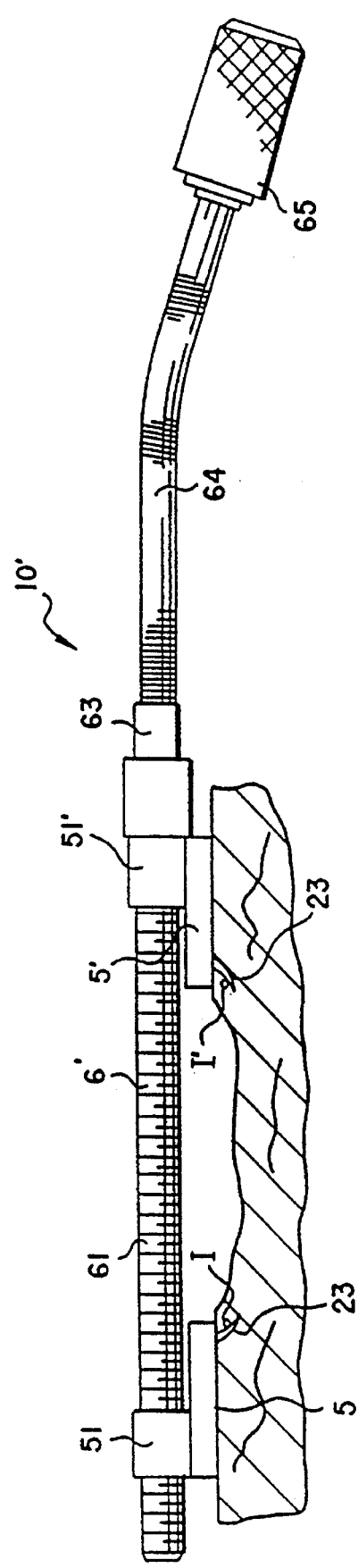
FIG.5
FIG.6

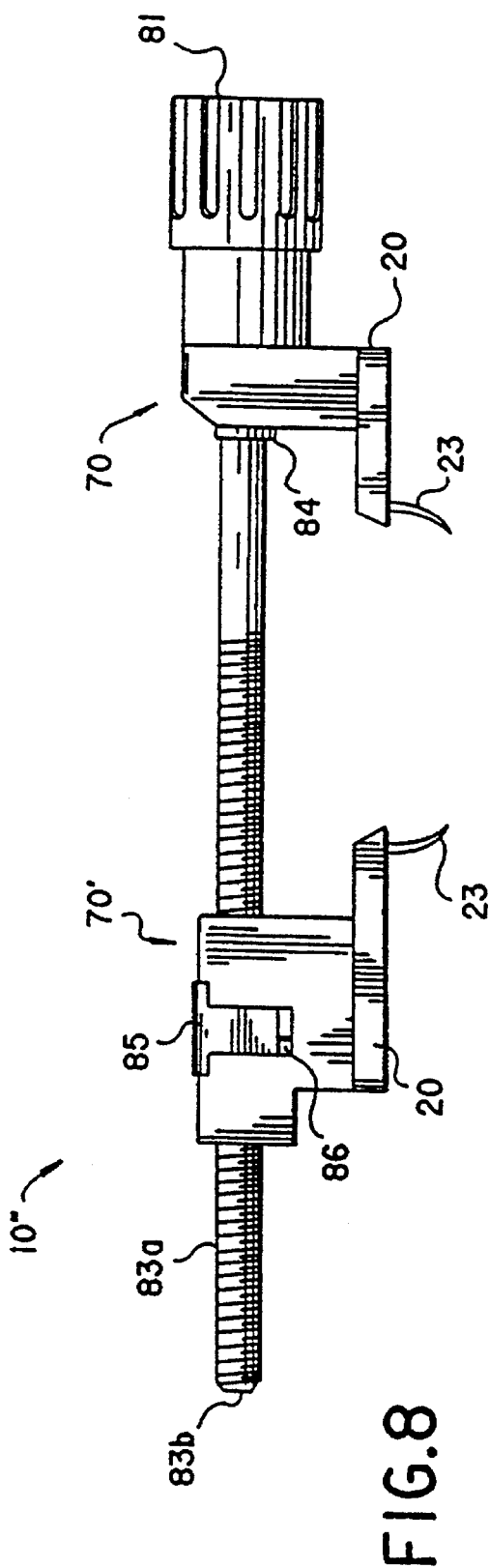
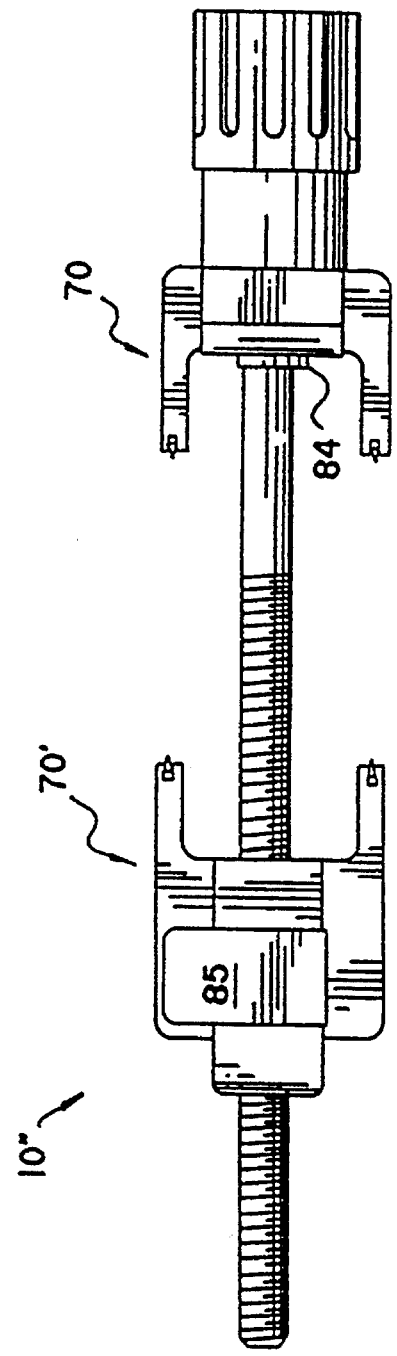
FIG.8
FIG.9

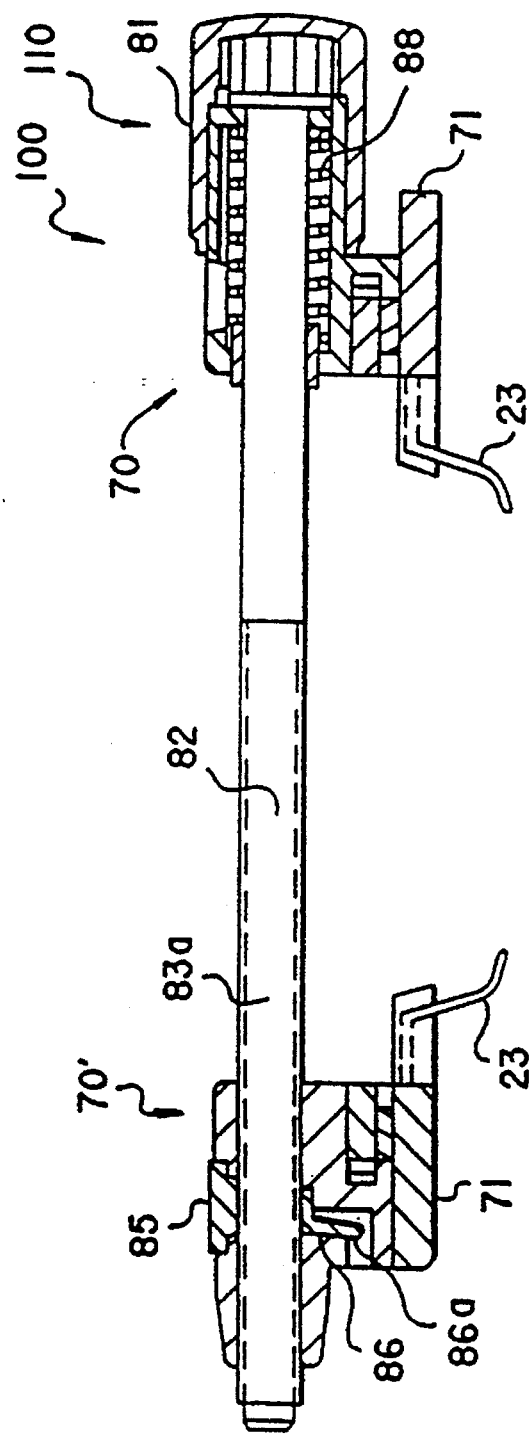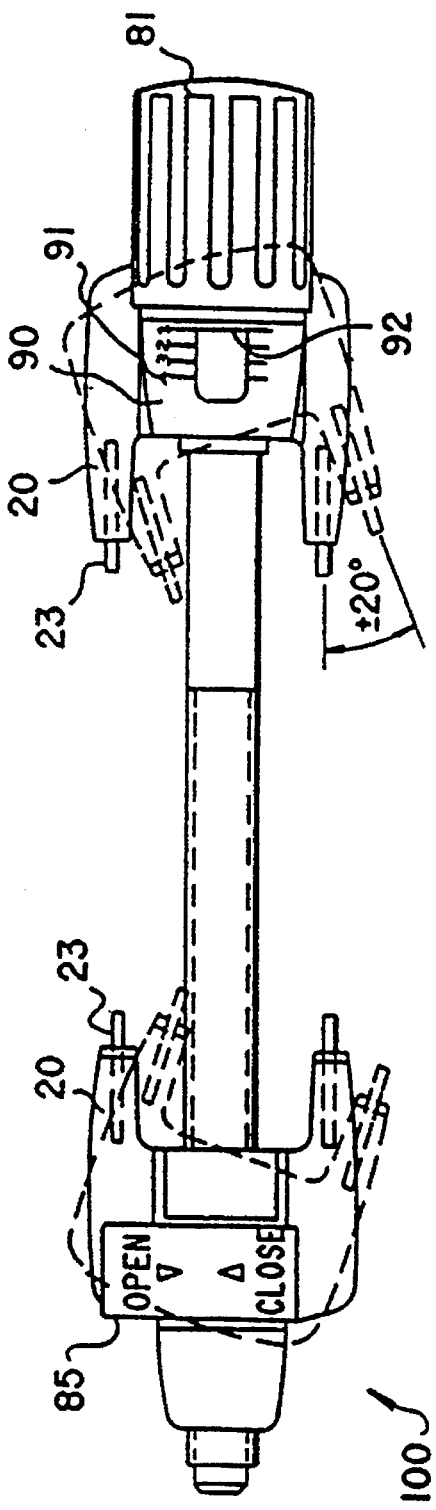
FIG.13
FIG.12

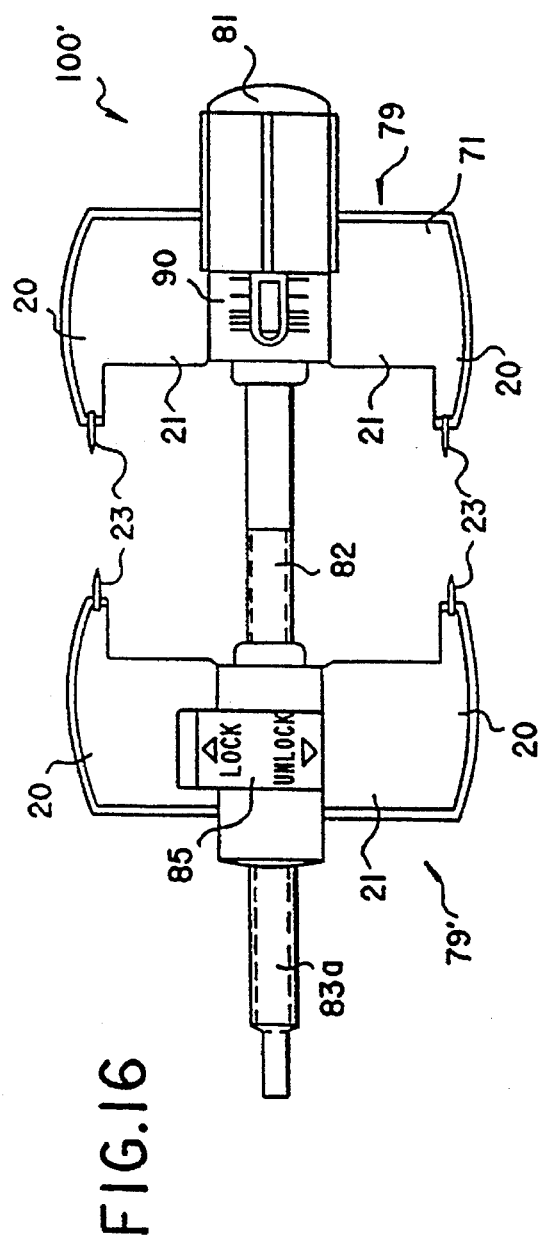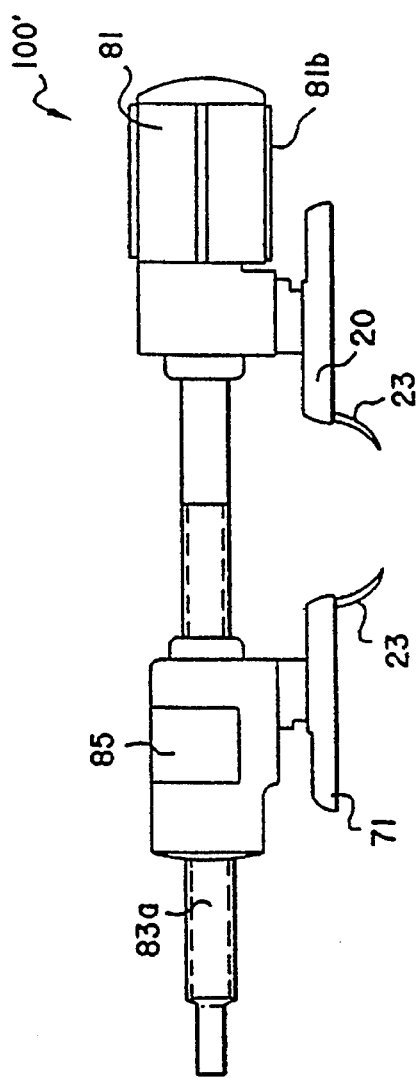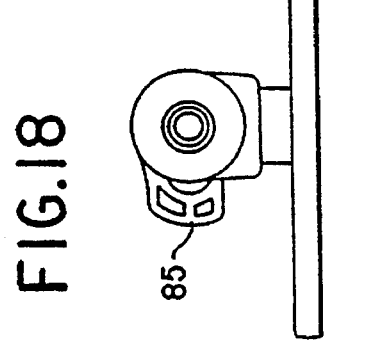

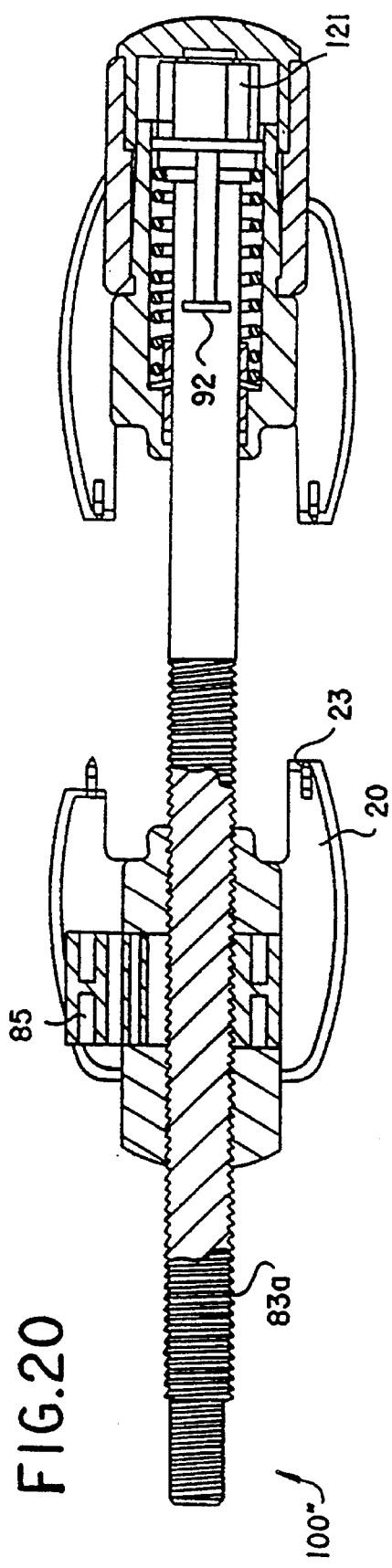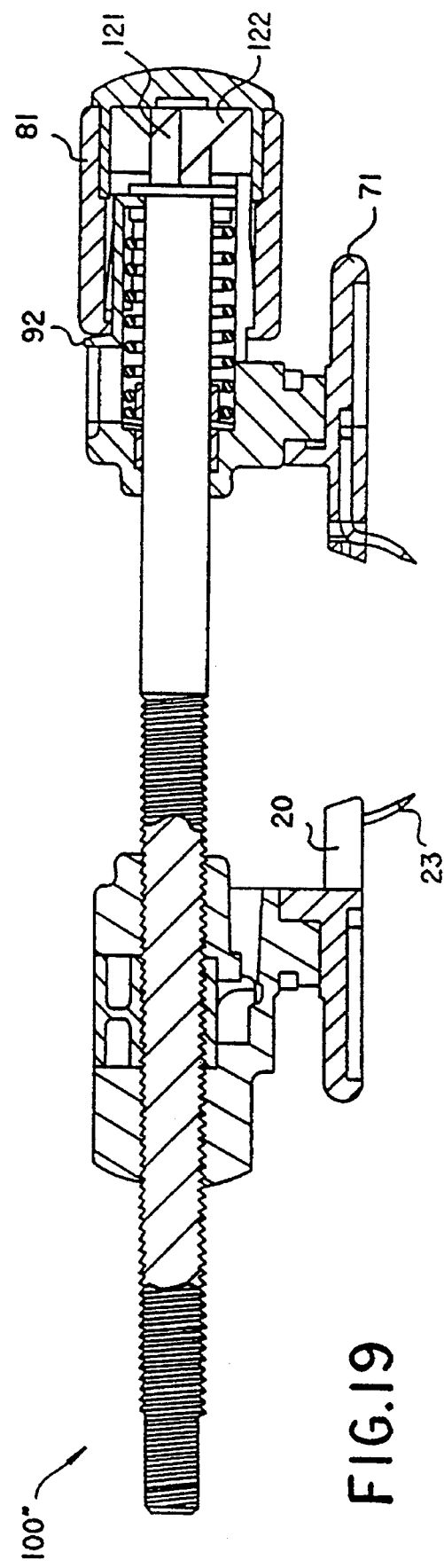
FIG.20
FIG.19

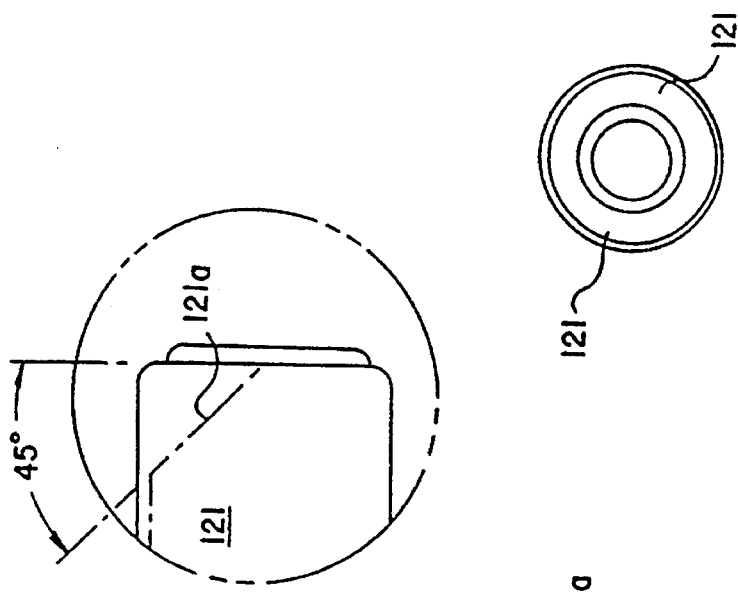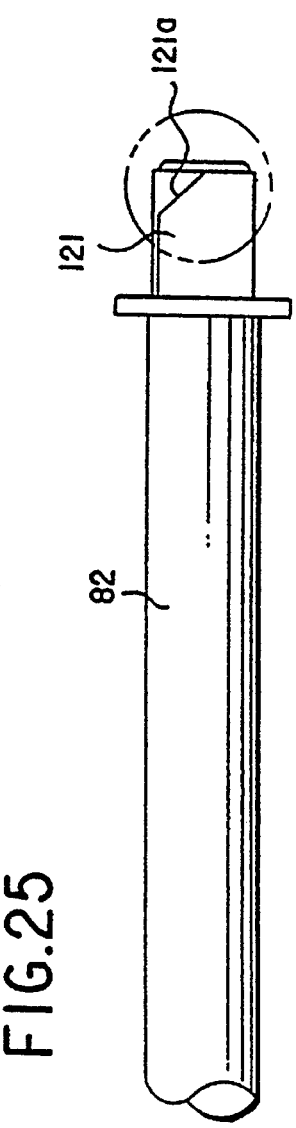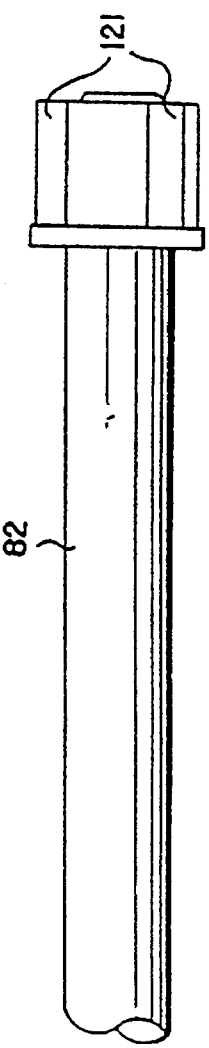

APPARATUS FOR THE CLOSURE OF WIDE SKIN DEFECTS BY STRETCHING OF SKIN

CROSS-REFERENCE TO RELATED APPLICATIONS

This is a continuation-in-part of U.S. patent application Ser. No. 07/835,636, filed Feb. 13, 1992, now U.S. Pat. No. 5,263,971; and is also a continuation-in-part of United States Design patent application Ser. No. 29/003,751, filed Dec. 3, 1992, now pending.

BACKGROUND OF THE INVENTION

1. Field of the Invention.

The invention relates to an apparatus for stretching skin to cover an open wound, and more particularly, to an apparatus for use before or during an operation for closure of skin defects or otherwise damaged skin areas.

2. Description of the Related Technology

U.S. Pat. No. 4,896,680 discloses a method and apparatus for stretching skin over a would by load cycling. A force may be applied on opposite skin margins during several periods interrupted by relaxation periods, so skin may be stretched over a wide area. A surgical Stretching apparatus according to that patent may include two pins for insertion into the skin along both edges of a wound.

The pins may be gradually pulled together by a flexible strap. The tension or pulling load on the pins may be applied in intervals to allow the collagen fibers of the skin to rearrange for further stretching. The pins may be substantially shaped as safety pins exhibiting a loop for attachment to a flexible strap. The strap may exhibit projections or apertures for engaging a ratchet-shaped device that nay hold the pins in forceful apposition.

A disadvantage of the above-described apparatus is manifest when the pins have been drawn together, as no space or room is provided for suturing the approximated skin margins. Another drawback resides in the rather crude manner for approximating the pins, i.e., manually pulling on the flexible strap, as the pulling force cannot be minutely controlled. Another drawback is the two pins grip only relatively narrow strips of skin along both edges, therefore, it is not possible to close a wide wound in a single pulling operation.

There exists a need for a skin closing or skin stretching device that closes a wide skin defect in a single pulling operation. There further exists a need for a skin closing apparatus that provides a visual or auditory indication of the tension or force applied to the wound margins during a pulling operation, and may limit the amount of force applied to the wound margins by disengaging a clutch mechanism.

SUMMARY OF THE INVENTION

It is an object of the invention to provide a skin stretching or closing apparatus which permits suturing of skin edges while the stretching apparatus is in situ without disturbing the suturing operation.

It is another object of the invention to permit insertion into the skin edges of long interdermal needles adapted to grip substantially the entire length of the wound or to permit shifting of the stretching mechanism along the wound edges thereby enabling the interdermal needles to be engaged in different locations.

It is a further object of the invention to permit either reusability or disposability of the apparatus and interdermal needles. According to one object of the invention, a device is provided which can be sterilized after use on one patient and subsequently reused on another patient. According to a second, alternative object, a device having limited reusability is provided which can be used multiple times on the same patient. A third alternative object is to provide a device which may be disposed after one use.

A preferred embodiment of a skin stretching apparatus may include two long interdermal needles for insertion under skin along the two edges of a wound to be closed; two U-shaped retaining members exhibiting a top surface, a bottom surface configured for placement close to the skin, and a sharp hook at the end of each leg of the U-shaped profile. A contracting mechanism may also be provided for pulling and approximating the two retaining members with their legs extending towards an open wound.

The retaining members may be placed behind the interdermal needles with respect to the wound location and in opposing alignment. The hooks of the retaining members may pierce the skin and engage an associated long interdermal needle in a position along the wound edges. The contracting mechanism may be designed to pull the retaining members slowly and gradually together so no damage to the skin area results. The U-shaped profile of the retaining member permits suturing of the skin edges, while the apparatus remains in position proximal to the wound due to the open spaces left between and on both sides of the two legs.

One embodiment of the contracting mechanism exhibits two contractor arms in parallel alignment and connected by a screw mechanism adapted to slowly bring together or approximate the two components by rotating the screw mechanism. One end of each contractor arm may be configured in the shape of a bar having a smooth, even cross-section adapted to carry a retaining member, so the retaining members are maintained in substantially opposite alignment along both sides of a wound, while allowing shifting of each retaining member along its respective bar.

The contractor arms may be slidably connected at their other ends by a smooth bar engaging bores in corresponding locations of the contractor arms with the two arms in parallel alignment. Each U-shaped retaining member exhibits two legs with outwardly bent hooks at a bottom surface of an end of each leg and connected by a longitudinally perforated flange mounted in a sliding fashion on a smooth bar of a contractor arm.

The two long interdermal needles may be inserted into the skin proximal to the wound margins. The skin closing apparatus is placed across the wound so the retaining members are positioned behind the skin margins. The hooks of the retaining members may be pressed through the skin into engagement with the interdermal needles. The screw mechanism may be rotated to slowly bring together or approximate the contractor arms and attached retaining members. The operation may be continued in intervals as described in the above patent.

A second embodiment of the apparatus also exhibits two U-shaped retaining members having forwardly bent hooks attached to the underside of the legs at their respective ends. According to this embodiment, each of the U-shaped retaining members exhibits a connecting flange attached to each of the legs. A lug defining a bore may protrude from a top surface of the connecting flange. One lug bore may exhibit a screw thread for engaging a rotatable screw that approximates the U-shaped retaining members, while bringing the retaining members and long interdermal needles together.

A preferred feature of the second embodiment includes a screw-threaded retaining member, a smooth-bored retaining member, and a screw exhibiting a collar at one end for engaging the smooth bore and the screw thread over its remaining length for engaging the screw-threaded retaining member. A drawback of this embodiment, when compared to the first embodiment, is an obstruction caused by the screw location that may hinder or prevent suturing of the wound area between the two legs.

Other contracting mechanisms may be provided for approximating the two retaining members. It should be further understood that a significant advantage of the invention resides in the shape of the two retaining members, which permits suturing of the wound margins while the apparatus is still in situ and continues to pull the wound margins together.

Other embodiments of the invention are described in detail below. Significant features of the invention include a clutch mechanism for preventing overtensioning of the device and a visual and/or auditory mechanism for indicating the force applied to the wound margins and also for indicating skin relaxation.

BRIEF DESCRIPTION OF THE DRAWINGS

FIG. 1 shows a top plan view of a first embodiment of a skin closing apparatus according to the invention positioned over an open skin wound.

FIG. 2 shows a partial section view of the apparatus taken along line 2—2 of FIG. 1.

FIG. 3 shows a partial section view of the apparatus taken along line 3—3 of FIG. 1.

FIG. 4 shows an end view of the apparatus taken along line 4—4 of FIG. 1.

FIG. 5 shows a top plan view of a second embodiment of a skin closing apparatus according to the invention.

FIG. 6 shows a side view in partial section of the apparatus of FIG. 5.

FIG. 8 shows a side view in elevation of the apparatus of FIG. 7.

FIG. 9 shows a top plan view of the apparatus of FIG. 7.

FIG. 12 shows a top plan view of a fourth embodiment of a skin closing apparatus according to the invention.

FIG. 13 shows a section view in elevation of the apparatus of FIG. 12.

FIG. 16 shows a top plan view of a fifth embodiment of a skin closing apparatus according to the invention.

FIG. 17 shows a side view in elevation of the apparatus of FIG. 16.

FIG. 18 shows a front end view of the apparatus of FIG. 16.

FIG. 19 shows a section view in elevation of a sixth embodiment of a skin closing apparatus according to the invention.

FIG. 20 shows a plan view in section of the apparatus of FIG. 19.

FIG. 24 shows a partial side view in elevation of a screw shaft or tension bar of the apparatus of FIG. 19.

FIG. 25 shows another partial side view in elevation of the screw shaft or tension bar of FIG. 24, which has been rotated 90°.

FIG. 26 shows an enlarged view of an end of the screw shaft or tension bar, as shown in FIG. 25.

FIG. 27 shows an end view of the screw shaft or tension bar of FIG. 25.

DETAILED DESCRIPTION OF THE PREFERRED EMBODIMENT

Figure 7:
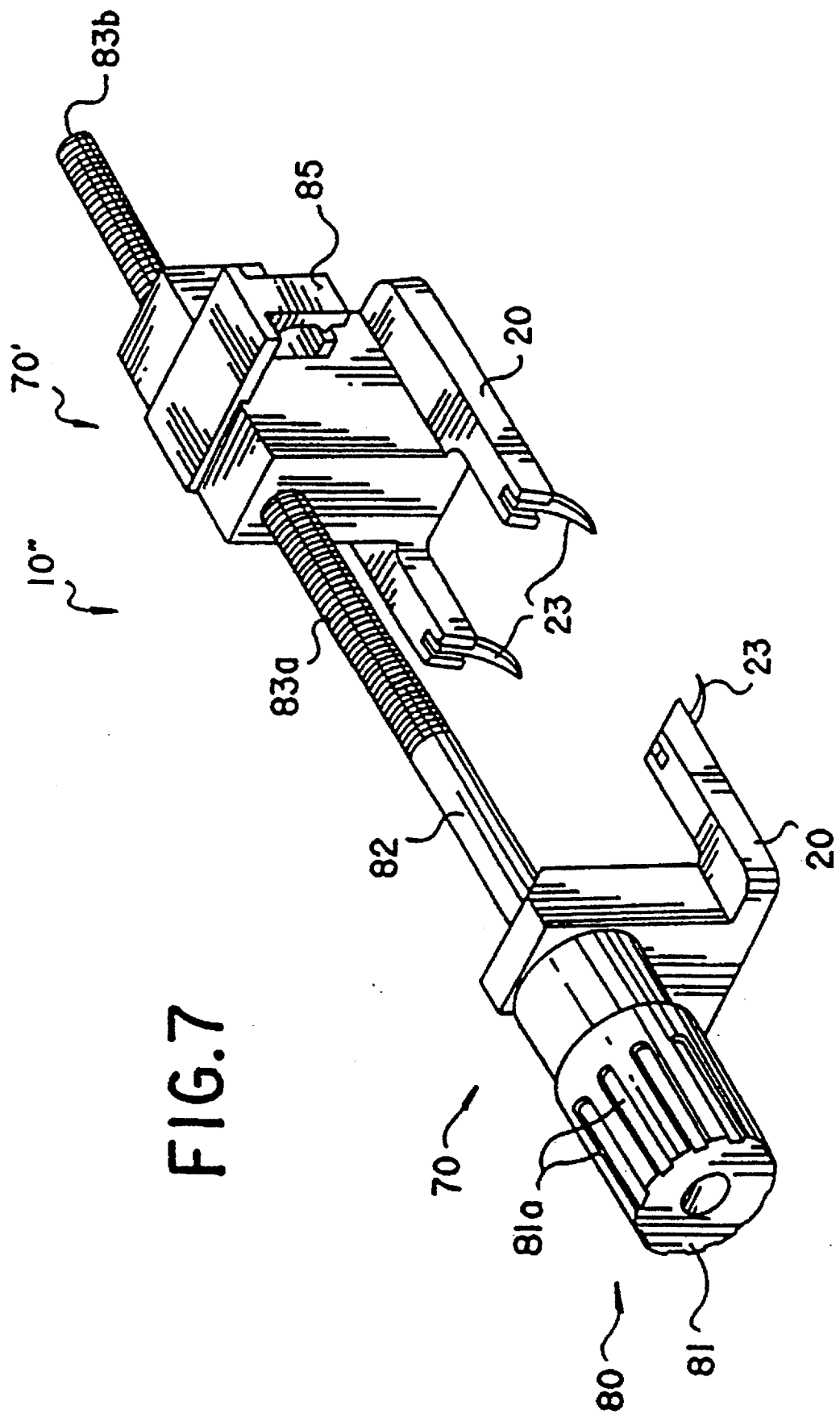
FIG. 7 shows a perspective view of a third embodiment of a skin closing apparatus according to the invention.
Figure 11:
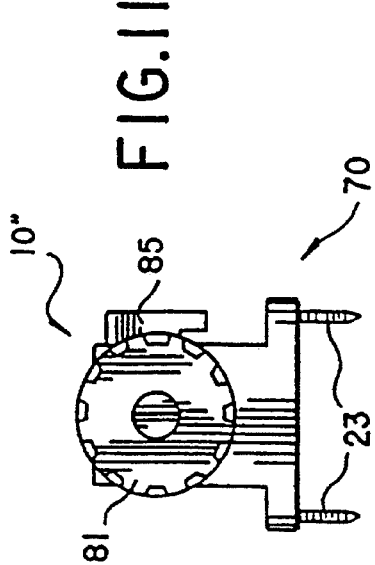
FIG. 11 shows a rear end view of the apparatus of FIG. 7.

FIGS. 1–4 show a skin closing or skin stretching apparatus according to the invention. Skin closing device 10 may be used with two long interdermal needles I, I'. Each interdermal needle may exhibit a head 1 and may be inserted under skin along wound margins as shown in FIGS. 1 and 2. The skin closing device may include two retaining members II, II' for engaging one of the two interdermal needles.

Each retaining member may exhibit a U-shaped profile, and two parallel, spaced-apart legs 20 connected by a flange 21 defining longitudinally directed bore 22 of preferably rectangular cross-section. Each of a plurality of forwardly extending hooks 23 may be connected to an underside of a retaining member. Each of the forwardly extending hooks may be located at an end of a leg 20 of a retaining member.

The hooks, which preferably exhibit a sharp point at the end, may pierce the skin and engage one of interdermal needles I, I' from a side remote from the wound. The retaining members are held in position by two contractor arms III, III' and are slidably mounted on bar-shaped ends 30 along rectangular bores 22. The contractor arms may be held in parallel alignment by a cylindrical bar 31 which extends through horizontal bores in lugs 32 at the other ends of the contractor arms.

A screw IV may pull or bring the contractor arms together and may extend through a screw-threaded bore in a lug 33 on a top surface of arm III and may further extend through a smooth bore in a lug 33' on a top surface of arm III'. Screw IV may exhibit a screw-threaded end 40, a collar 41 abutting lug 33' of contractor arm III' and a handle or knob 42 attached to screw IV by a flexible tube or helical spring 43. By rotating handle 42 the screw-threaded end in engagement with the thread in the lug 33 may pull arms III, III' to each other whereby retaining members II, II' contract the wound margins by hooks 23 and interdermal needles I, I'.

As described in U.S. Pat. No. 4,896,680, a skin closing operation may performed in several stages to allow the skin to stretch in a gradual manner during intervals between the stretching stages. After the skin defect or wound margins have been brought into contact, the wound may be sutured in a manner known to the art, whereby it is evident that legs 20 do not interfere with the operation, as legs 20 are remote from the margins.

FIGS. 5 and 6 show a second embodiment of a skin closing apparatus 10'. Retaining members 5, 5' are approximated or brought together by a screw 6. The retaining members, which are substantially similar to the retaining members of FIGS. 1 and 2, may exhibit perforated lugs 51, 51' on their respective top surfaces. Lug 51 may define a perforation such as screw-threaded bore and lug 51' may define a perforation such as a smooth bore.

Screw 6 exhibits a screw-threaded end 61 cooperating with the screw thread in lug 51 of retaining member 5, a smooth portion (not shown) rotating in lug 51', a collar 63 abutting lug 51' and a flexible operating portion 64 terminating in a knob or handle 65. The skin contracting operation is similar to that described for the above embodiment, however, screw 6 somewhat obstructs the suturing operation.

FIGS. 7–11 show a third embodiment of a skin closing apparatus 10", which exhibits retaining members 70, 70' and a screw 82 for applying skin stretching forces. This embodiment may also be used with two long interdermal needles that are inserted into the skin for distributing closing forces along edges of a wound. A significant advantage provided by the long interdermal needles is the uniform distribution of force across a wide area of skin. Retaining members 70, 70' also exhibit skin insertion elements or hooks 23 connected to each leg 20 for a total of four which engage the long interdermal needles during a skin stretching operation.

Retaining member 70 may be configured as a force supplying retaining member and may exhibit a U-shaped profile. Retaining member 70' may be located opposite a skin defect from retaining member 70 and may also exhibit a U-shaped profile. A contracting mechanism 80 for approximating the retaining members may also be provided.

The contracting mechanism may include a large knob 81 for applying a force and may be located proximal to retaining member 70. The knob may include grooves 81a and/or ridges 81b (see FIG. 17) for facilitating a user's manipulation of the knob. The contracting mechanism may also include a screw shaft or tension bar 82 exhibiting a screw-threaded portion 83a and a distal screw end 83b.

According to the preferred embodiment, the screw shaft exhibits rigidity so bending along the screw axis is minimized. A fiberglass reinforced material may be used, which provides extra rigidity, that is not available from unreinforced material. It is also preferred to use a teflon or silicone filled plastic material. Teflon is preferred as it provides lubrication and keeps the threads running easily and so limits the amount of hysteresis or friction.

Figure 10:
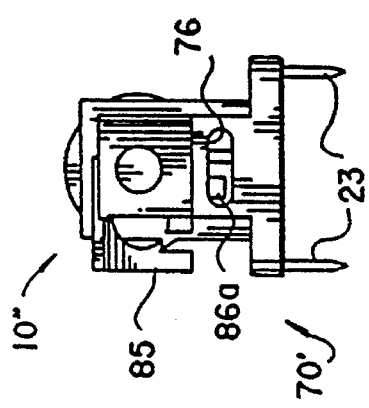
FIG. 10 shows a front end view of the apparatus of FIG. 7.

Retaining member 70' may also exhibit a reversible lock 85 for releasably locking the retaining member to the screw. The lock 85 exhibits a threaded partial bore for defining a threaded connection and a larger smooth partial bore for allowing the retaining member 70' to slide freely along the tension bar 82. The user may select the engaged position by sliding the lock 85 to engage the threaded partial bore with the screw-threaded portion 83a of the tension bar. The free position is selected by sliding the lock 85 so that the larger smooth partial bore is positioned circumferentially about the screw-threaded portion 83a of the tension bar 82. As best seen in FIG. 10, lock 85 may also include a lock shaft 86 (see FIG. 15) and a lock shaft finger 86a that slides in a slot 76 of retaining member 70'. The reversible lock advantageously allows the user to disengage the retaining members in a quick manner and also to reengage the retaining members in a threaded connection.

The lock exhibits a threaded portion, which allows one to lock the retaining members together. The lock may also be biased i.e., by the resilience of the material selected, so the lock may stay in either the closed or open position.

FIGS. 12–15 show a fourth embodiment of the skin closing apparatus 100, which exhibits retaining members 70, 70' and a screw 82 for applying skin stretching forces. It is also contemplated that two long interdermal needles may be inserted into the skin and may distribute closing forces along edges of a wound when used with this embodiment. An advantage of the long interdermal needles is the uniform distribution of force across a wide area of skin. Retaining members 70, 70' also exhibit skin insertion elements or hooks 23 connected to each leg 20 for a total of four which engage the long interdermal needles during a skin stretching operation.

This embodiment also exhibits retaining members having swiveling or pivotal base segments 71. As shown in FIG. 12, the preferred amount of pivoting is a rotational motion of about 40°, i.e., about ±20° from a detent mechanism or centering the pivotal base segment about a reference position of the retaining member.

It is also contemplated for the pivotal base segments 71 to pivot throughout a full circular motion of 360°. An advantage realized by providing swiveling or pivotal base segments is that such rotary motion allows the device to conform to irregular force loading, irregular skin motion, or irregular wound margins, thereby avoiding uneven distribution of forces or dislocation of the device. The rotary or pivotal motion of the retaining members allows the device to be compliant with the natural imbalance of the forces encountered in the wound closing.

A force level indicator 90 may also be provided. The force level indicator indicates the force applied along the margins of the skin defect by the contracting mechanism. The force level indicator may include a pointer 92 and a scale using a color scheme or numerals to indicate the varying levels of force applied.

In a preferred embodiment, an objective scale such as numerals 91 represent the different level of force applied to the wound margins. Alternatively, a subjective numerical or a scale color scheme scale, such as green for low level force, yellow for a moderate, force application and red for a high force level may be provided.

Figure 14:
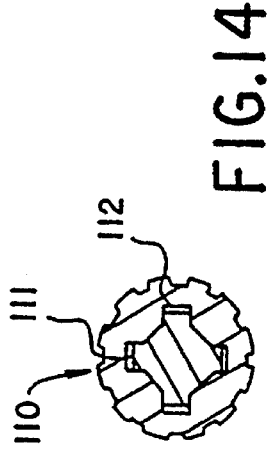
FIG. 14 shows a section view in elevation through a clutch of the apparatus of FIG. 12.

FIGS. 13 and 14 show a fourth embodiment including a clutch 110 for limiting the forces that may be applied by the contracting mechanism. For the purposes of this application, Applicants define a clutch as any mechanical, electromagnetic or hydraulic or other device for engaging a first rotatable element or shaft to, or disengaging the first element from a second rotatable element or shaft. Accordingly, the clutch may be configured as a frictional clutch or a matching spline system located inside knob 81 and the shaft of the screw.

A compression spring 88 may urge male spline 111 toward female spline 112. According to the preferred embodiment the compression spring is configured so the splines disengage, when a force of about 2.5 kilograms or somewhat higher is applied.

The female spline may be configured as a recess complementing the shape of the male spline and defined by the walls of the knob. As a force or torque is applied to the knob, the indicator which fits through the apparatus and protrudes from the torquing knob, moves forward indicating that larger and larger forces are being applied to the wound margins.

As the skin stretches and those forces decrease, the indicator retracts along the scale and may move along the numerals from 4 to 1. Screw 82 connects the retaining members together so tension is applied to the wound margins as the interdermal needles and retaining members are brought together.

Figure 15:
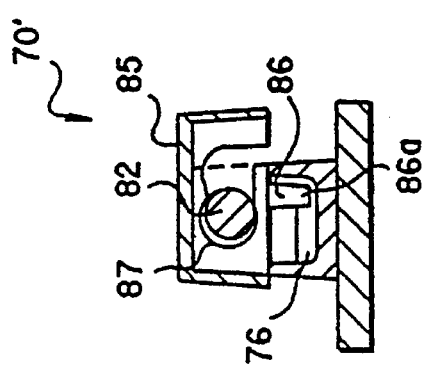
FIG. 15 shows a section view in elevation through a retaining member of the apparatus of FIG. 12.
Figure 21:
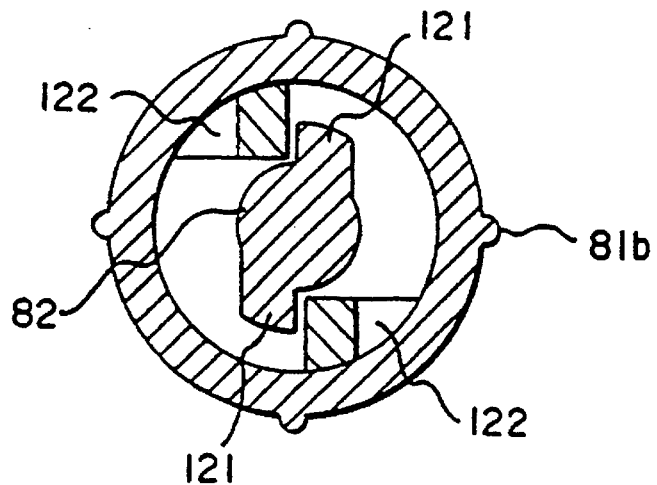
FIG. 21 shows a section view in elevation through a clutch of the apparatus of FIG. 19.
Figure 22:
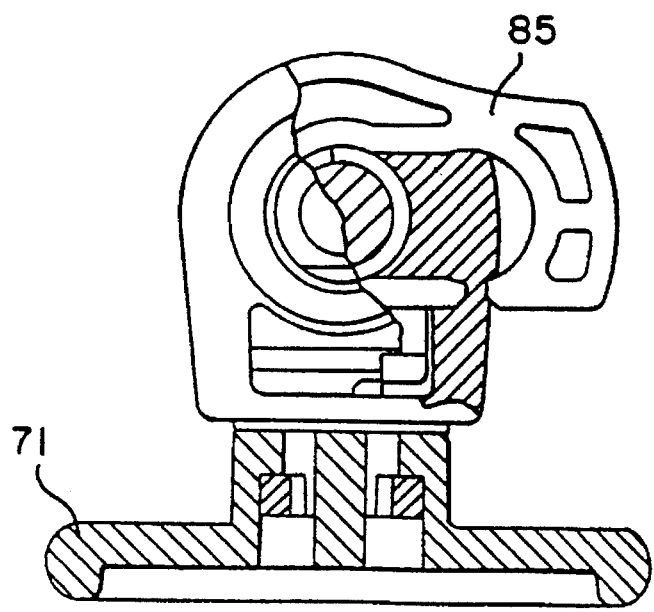
FIG. 22 shows a front view in partial section of the apparatus of FIG. 19.

Retaining member 70' may also exhibit releasable lock 85 for providing a threaded connection to the screw. Lock 85 may be configured as a resilient latch which engages the thread and exhibits a resilient structure to remain in either the locked or unlocked position. The resilient nature of lock and lock shaft finger 86a retain the lock within the retaining member. As shown in FIG. 15, finger 86a may be a resilient structure that snaps into engagement with a wall defining slot 76.

This embodiment is preferably sterilized using gamma sterilization. Although conventional sterilization techniques, i.e., ETO sterilization, may also be utilized.

FIGS. 16–18 show a fifth embodiment of the skin closing apparatus 100', which exhibits retaining members 79, 79' and a screw 82 for applying skin stretching forces. Two long interdermal needles may be inserted into the skin and may transmit closing forces to the skin, when used with this embodiment. Retaining members 79, 79' also exhibit skin insertion elements or hooks 23 connected to each leg 20. According to the preferred embodiment, knob 81 exhibits ridges or protrusions 81b for enhancing tactile sensation, especially when the surgeon is wearing gloves.

This embodiment also exhibits retaining members having swiveling or pivotal base segments 71 with the preferred amount of pivoting is a rotational motion of about 40°, i.e., about ±20° from a central or reference position. This embodiment differs from the previous embodiments as the pivotal base segments are "wide" to eliminate the need for using multiple devices or a single device multiple times to close a skin area.

According to the preferred embodiments shown in FIGS. 12–15 the width of each retaining member is between 20 and 40 millimeters. In the wide embodiment shown in FIGS. 16–18, the greater width of each retaining member (between 40 and 80 millimeters) provides additional stability. Both embodiments are preferably sterilized using gamma sterilization. Although conventional sterilization techniques, i.e., ETO sterilization, may also be utilized.

FIGS. 19–27 show a sixth embodiment of the skin closing apparatus 100", which is substantially similar to the embodiment of FIGS. 12–15. This embodiment has an improved clutch mechanism which exhibits two stationary splines 121 that are located in the knob and exhibit inclined contact surfaces.

Screw 82 exhibits two axially movable splines with inclined surfaces. The advantage of this clutch element is seen when the splines reengage during skin relaxation. Due to the inclined surfaces, the splines may automatically realign in the initial position. In contrast to this improved clutch, the prior clutch may exhibit misalignment problems if the male and female splines are not centered with respect to each other during realignment.

Figure 23:
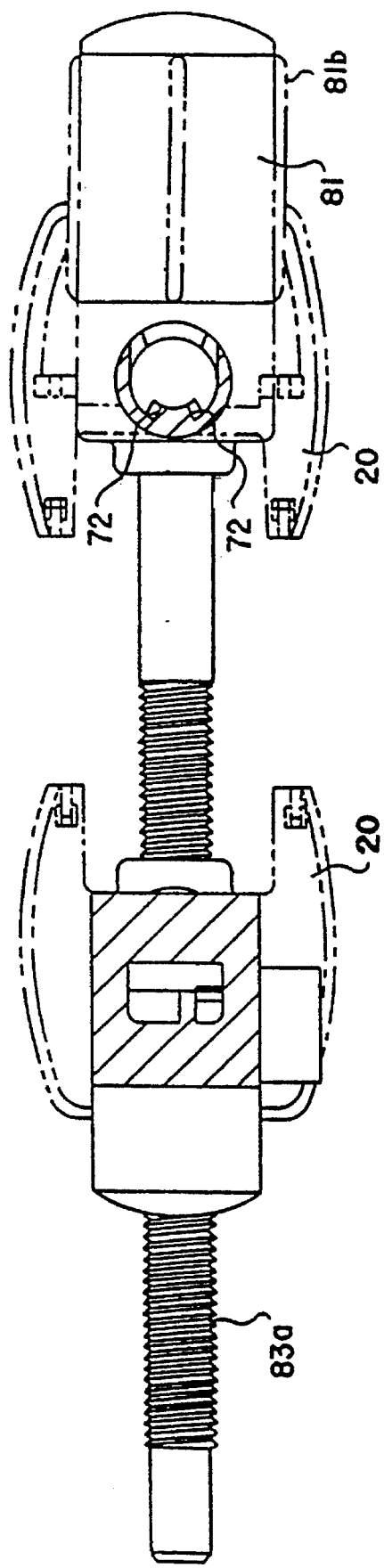
FIG. 23 shows a top plan view in partial section of the apparatus of FIG. 19.

FIG. 23 shows a sectional view of an apparatus with stops 72 which limit the rotational movement of the pivotal base segments. FIGS. 24–27 show screw shaft 82, with the thread omitted for purposes of clarity only, in enlarged detail. The splines 121 may include oblique contact surfaces 121a, which are preferably inclined at 45° angles.

Figure 28:
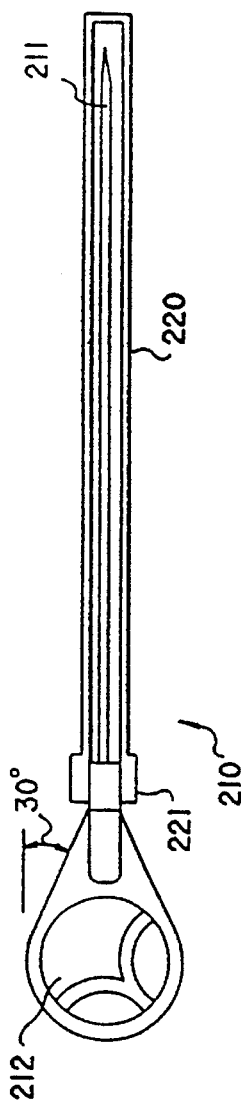
FIG. 28 shows a top plan view of another embodiment of a long interdermal needle according to the invention.
Figure 29:
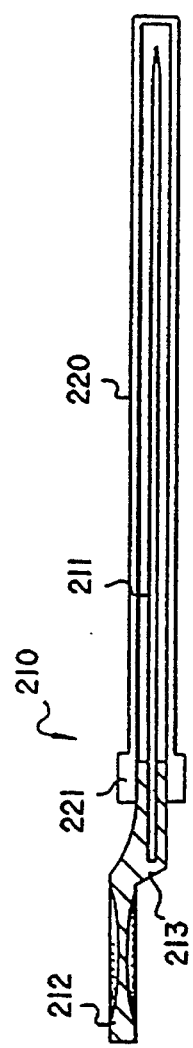
FIG. 29 shows a partial section view in elevation of the long interdermal needle of FIG. 28.

FIGS. 28 and 29 show the preferred embodiment of the long interdermal needles, which may exhibit a cross-section of three edges or five edges. Each interdermal needle 150 exhibits a straight shaft 151 with a tapered point 151a.

According to the preferred embodiment, the interdermal needle is made of surgical steel. The straight shaft may be connected to a handle 152 that includes an offset portion 153. The handle and shaft may be connected by gluing or welding. The offset handle facilitates manipulation and insertion of the long interdermal needles. A protective covering 160 may be provided. The covering may exhibit wings or extensions 161 for easy disassembly of the protective covering from the long interdermal needle.

Figure 30:
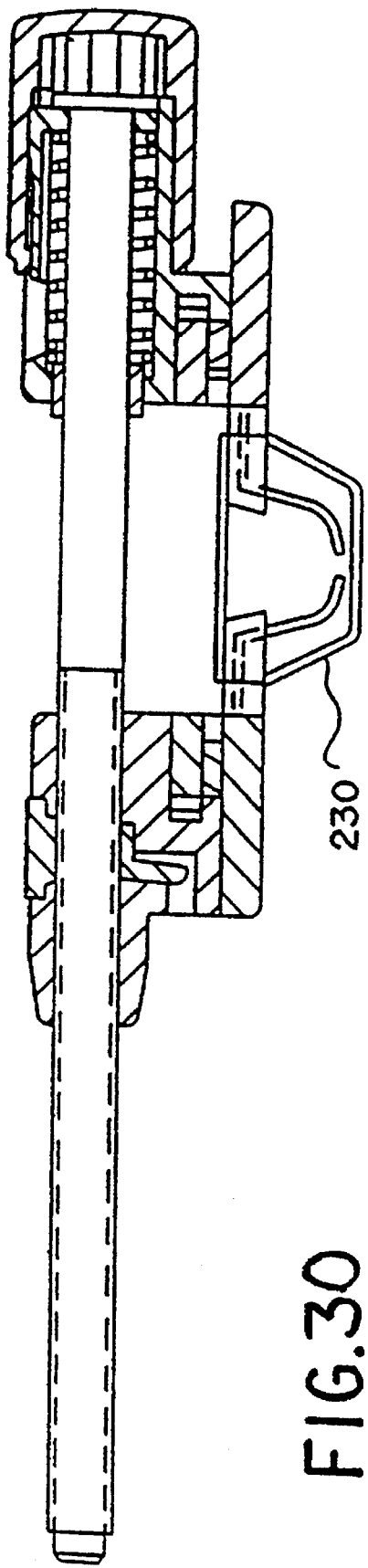
FIG. 30 shows a top plan view of an apparatus according to the invention with a protective covering.
Figure 31:
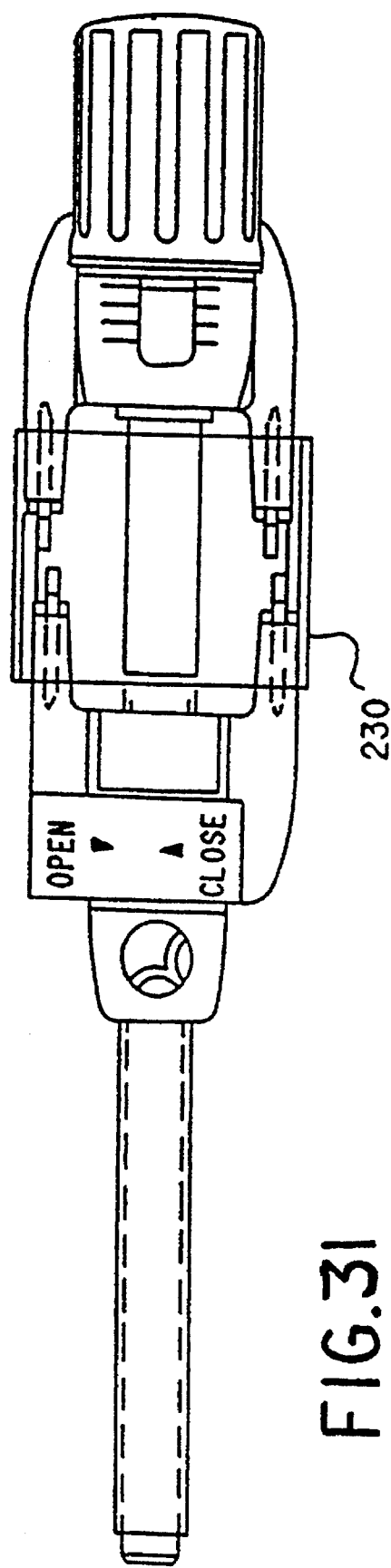
FIG. 31 shows a section view in elevation of the apparatus and protective covering of FIG. 30.

FIGS. 30 and 31 show an embodiment of the skin stretching device configured with a protective covering 170. According to the preferred embodiment a clear plastic cover is provided so the user may see the skin piercing elements. The cover also protects the skin piercing elements during handling and shipping. Further, the cover protects the surgeon from injury.

Figure 32:
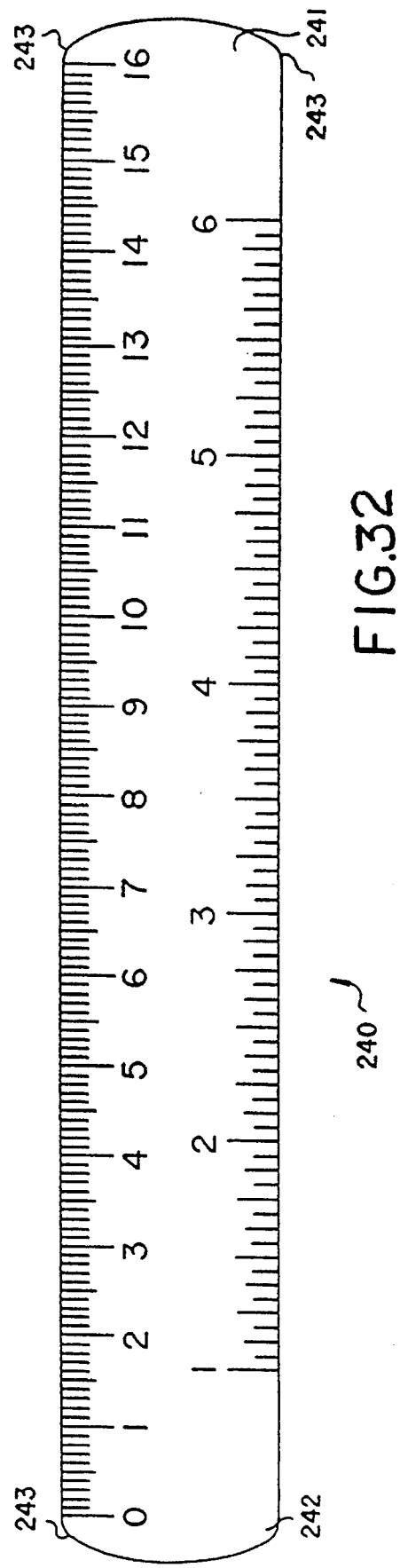
FIG. 32 shows a top plan view of a retractor according to the invention.

FIG. 32 shows a retractor 180 for use with the skin closing device. Preferably, the retractor is substantially the same length of the skin stretching device and enhances placement and alignment of the device about the skin defect. The retractor should have atraumatic ends 181, 182, which may be configured with curved edges 183.

The device may also be configured with blunt needles or hooks in lieu of skin piercing elements. A sharp stylet may be used to puncture the skin. The blunt needles of the retaining members may then be inserted into the punctured areas. The blunt needle configuration provides an important safety feature as the surgeon may be cut by the skin piercing elements and infected with a patient's body fluids. The device and use of the device is otherwise identical to the above-described embodiments.

According to the preferred embodiment, the screw shaft is made of 30% glass fiber and 15% PTFE filled polycarbonate. The indicator and bushing are made of polyamide (nylon) 6/6. The skin insertion elements and long interdermal needles are made of surgical stainless steel, and all other parts are made of "Lexan" polycarbonate.

In summary, the device is contemplated for use with wide wounds or skin defects. A large wound may be caused by a gunshot, a different trauma, surgery, or a cancer and may require removal. After excising the margins of a large wound to be closed, if necessary, a surgeon would insert the two long interdermal needles in the opposing edges of the skin.

Next, the surgeon would place the two retaining members on opposite sides of the wound, while hooking the skin insertion elements on either end underneath the long interdermal needles. It should be noted that the long interdermal needles may be inserted deeper than the skin level, i.e., into the fascia. It should also be noted that the two retaining members may be disassembled prior to placement about the wound and subsequently reassembled prior to approximation. I Once both ends of a retaining member are hooked the surgeon can quickly bring the ends together until a certain amount of resistance to closing the tissue is encountered.

At that time, the reversible lock may be snapped into the locked threaded position so the retaining members are connected in threaded engagement. The surgeon may begin turning the knob and applying stretching forces until reaching a recommended force, as indicated by a number on the scale of the force level indicator.

An advantage of the invention is realized in the event that the surgeon continues to turn the knob. The force applied is at a maximum level and cannot be exceeded. The force will not increase as the clutch has disengaged. During the application of force the spring has compressed while the retaining members are being brought together. And the indicator moves along the scale, the surgeon may visualize the application of increasing force.

The inventors note that a visualization also occurs when the spline disengages, as the indicator no longer moves to a higher value. The surgeon also receives tactile feedback that there is no more force being applied. In this regard the device is self-regulating: According to the preferred embodiment, the skin stretching device has a certain constant spring rate, Hooke's constant for the spring. The visco-elastic properties of the skin allows the skin to stretch, and the compressed spring expands while returning essentially to its original, rest position.

The retaining members also come together simultaneously with the spring expansion. The indicator shows that the force level is decreasing. The indicator shows movement, i.e., so an observer can see that the device is still working. The clutch also reengages so the surgeon may perform additional skin stretching operations. These operations are repeated in intervals until the skin comes together. The spring and the force limiting action significantly control stretching operation. As the skin, relaxes the device returns essentially to its original, rest position. It's very easy to visualize the stretching and relaxation of the skin. In that regard the device functions as a feedback system.

It is also contemplated for a wound of significant dimensions to use the device to close an area of skin, apply sutures to that area and reposition the device on another part of that, wound or on another wound on the same patient. It is further contemplated to use multiple devices on a single patient or wound simultaneously.

The illustrated embodiments are shown by way of example. The spirit and scope of the invention is not to be restricted by the preferred embodiments shown.

What is claimed is:

1. A method of closing a wide skin defect comprising the steps of:
   inserting interdermal needles into skin along margins of the skin defect;
   locating retaining members about the skin defect proximal to the interdermal needles;
   applying force to a contracting mechanism through a force limiting element so the retaining members engage the interdermal needles and bring one margin of the skin defect toward another margin of the skin defect without exceeding a predetermined force.

2. The method of closing a wide skin defect according to claim 1, wherein said step of locating retaining members about the skin defect proximal to the interdermal needles further comprises the step of:
   piercing skin with skin piercing elements attached to the retaining members so the skin is pierced simultaneously with the step of locating retaining members about the skin defect.

3. The method of closing a wide skin defect according to claim 1, wherein said step of locating retaining members about the skin defect proximal to the interdermal needles further comprises the steps of:
   piercing skin with skin piercing elements; and
   locating skin insertion elements attached to the retaining members in pierced skin areas.

4. The method of closing a wide skin defect according to claim 1, further comprising the steps of:
   observing skin relaxation as indicated by decreasing values on a force level indicator; and
   reapplying force to a contracting mechanism so the retaining members engage the interdermal needles and bring one margin of the skin defect toward another margin of the skin defect, when a predetermined force level is indicated on the force level indicator.

5. A skin closing apparatus for closing skin defects comprising:
   at least two retaining members, each of said retaining members exhibiting a coaxial bore and a plurality of skin insertion elements for insertion into the skin along margins of the skin defect;
   a substantially rigid contracting mechanism extending through each said coaxial bore and connecting said retaining members; and
   a clutch operatively engaging said contracting mechanism and configured so a force applied along the margins of the skin defect by said contracting mechanism is limited to a predetermined value.

6. The skin closing apparatus according to claim 5, wherein said contracting mechanism exhibits a plurality of contractor arms in substantially parallel alignment, each of said contractor arms supporting one of said retaining members in a sliding arrangement.

7. The skin closing apparatus according to claim 6, wherein each of said contractor arms exhibits a straight, smooth bar at one end, each of said retaining members further exhibiting a retaining member support bore configured so said contractor arm bar passes through said retaining member support bore.

8. The skin closing apparatus according to claim 6, wherein one of said contractor arms exhibits a contractor arm smooth bore, and another of said contractor arms exhibits a contractor arm screw-threaded bore.

9. The skin closing apparatus according to claim 8, further comprising a screw connecting said contractor arms and exhibiting a screw-threaded portion engaging said contractor arm screw-threaded bore.

10. The skin closing apparatus according to claim 8, wherein each of said contractor arms exhibits a plurality of lugs, each of said lugs defining one of said contractor arm bores.

11. The skin closing apparatus according to claim 6, further comprising a cylindrical bar, wherein each of said contractor arms further exhibits an alignment bore; said cylindrical bar extending through said alignment bores.

12. The skin closing apparatus according to claim 5, wherein each of said retaining members exhibits at least two legs and a flange connecting said legs; said coaxial bore is a flange bore extending through said flange and exhibiting an axis in substantially parallel alignment with axes of said legs.

13. The skin closing apparatus according to claim 12, wherein one of said flange bores is a threaded flange bore, another of said flange bores is a smooth flange bore, said contracting mechanism comprising at least a screw extending through said flange bores.

14. The skin closing apparatus according to claim 5, wherein said at least two retaining members further comprise two U-shaped retaining members, each of said U-shaped retaining members exhibits two legs and a flange connecting said legs.

15. The skin closing apparatus according to claim 5, further comprising a plurality of interdermal needles for engagement by said skin insertion elements.

16. The skin closing apparatus according to claim 15, wherein said plurality of interdermal needles comprises two interdermal needles.

17. The skin closing apparatus according to claim 5, wherein said clutch is a frictional clutch.

18. The skin closing apparatus according to claim 5, wherein said clutch exhibits a male spline and a female spline defining a recess configured to receive said male spline.

19. The skin closing apparatus according to claim 5, wherein a distance between said retaining members defines an axis, said clutch exhibits a plurality of splines, one of said splines configured as an axially stationary spline, another of said splines configured as an axially movable spline.

20. The skin closing apparatus according to claim 19, wherein each of said splines exhibits an oblique contact surface.

21. The skin closing apparatus according to claim 5, further comprising a force level indicator connected to said contracting mechanism and for indicating the force applied along the margins of the skin defect.

22. A skin defect closing apparatus comprising:
   a plurality of retaining members, each of said retaining members exhibiting:
      at least two legs,
      a flange connecting said legs and exhibiting a flange bore located between said legs,
      a plurality of blunt skin insertion elements, each of said skin insertion elements protruding from a surface of one of said legs; and
   a contracting mechanism connecting said retaining members and engaging one of said flange bores, said contracting mechanism configured to approximate said retaining members.

23. The skin defect closing apparatus according to claim 22, wherein each of said retaining members is configured so said legs are in parallel alignment.

24. The skin defect closing apparatus according to claim 22, further comprising two interdermal needles, each of said interdermal needles is configured for insertion underneath skin proximal to a margin of a skin defect, each of said skin insertion elements engaging one of said interdermal needles.

25. The skin defect closing apparatus according to claim 22, wherein said plurality of retaining members comprises two retaining members.

26. The skin defect closing apparatus according to claim 22, wherein said contracting mechanism comprises at least a screw.

27. The skin defect closing apparatus according to claim 26, wherein one of said flange bores is a screw-threaded flange bore, said screw engaging said screw-threaded flange bore.

28. The skin defect closing apparatus according to claim 26, wherein one of said retaining member flange bores is a smooth bore, said screw exhibits a collar configured to contact said retaining member exhibiting said smooth bore, said screw extending through said smooth bore.

29. The skin defect closing apparatus according to claim 22, wherein said at least two retaining members further comprise two U-shaped retaining members, each of said U-shaped retaining members exhibits two legs and a flange connecting said legs.

30. The skin defect closing apparatus according to claim 22, further comprising a plurality of interdermal needles configured so said retaining members engage said interdermal needles, when said contracting mechanism approximates said retaining members.

31. The skin defect closing apparatus according to claim 30, wherein said plurality of interdermal needles comprises two interdermal needles.

32. The skin defect closing apparatus according to claim 30, wherein each of said plurality of interdermal needles exhibits a handle and a straight interdermal needle shaft connected to said handle.

33. The skin defect closing apparatus according to claim 32, wherein said handle exhibits a portion offset from said straight interdermal needle shaft.

34. The skin defect closing apparatus according to claim 22, further comprising a force level indicator connected to said contracting mechanism and for indicating the force applied along the margins of the skin defect.

35. The skin defect closing apparatus according to claim 34, wherein said force level indicator exhibits a plurality of numerals, each of said numerals representing a different level of force applied along the margins of the skin defect.

36. The skin defect closing apparatus according to claim 22, wherein said contracting mechanism exhibits a clutch configured so a force applied along the margins of the skin defect by said contracting mechanism is limited to a predetermined value.

37. The skin defect closing apparatus according to claim 36, wherein said clutch is a frictional clutch.

38. The skin closing apparatus according to claim 22, wherein each of said blunt skin insertion elements is a blunt hook.

39. A skin defect closing apparatus comprising:
   a plurality of retaining members, each of said retaining members exhibiting:
      at least two legs,
      a flange connecting said legs and exhibiting a flange bore located between said legs,
      a plurality of skin insertion elements, each of said skin insertion elements protruding from a surface of one of said legs;
   a contracting mechanism comprising at least a screw connecting said retaining members and engaging one of said flange bores, said contracting mechanism configured to approximate said retaining members; and
   a reversible lock disposed on one of said plurality of retaining members, said lock having at least a locking threaded element and configured so said locking threaded element engages said screw when said reversible lock is in a locked position.

40. A skin defect closing apparatus comprising:
   a plurality of retaining members, each of said retaining members exhibiting:
      at least two legs,
      a flange connecting said legs and exhibiting a flange bore located between said legs,
      a plurality of skin insertion elements, each of said skin insertion elements protruding from a surface of one of said legs; and
   a contracting mechanism connecting said retaining members and engaging one of said flange bores, said contracting mechanism configured to approximate said retaining members and exhibiting a clutch configured so a force applied along the margins of the skin defect by said contracting mechanism is limited to a predetermined value, said clutch exhibiting a male spline and a female spline defining a recess configured to receive said male spline.

41. A skin defect closing apparatus comprising:
a plurality of retaining members, a distance between each of said retaining members defining an axis, each of said retaining members exhibiting:
at least two legs,
a flange connecting said legs and exhibiting a flange bore located between said legs,
a plurality of skin insertion elements, each of said skin insertion elements protruding from a surface of one of said legs; and
a contracting mechanism connecting said retaining members and engaging one of said flange bores, said contracting mechanism configured to approximate said retaining members and exhibiting a clutch configured so a force applied along the margins of the skin defect by said contracting mechanism is limited to a predetermined value, said clutch exhibiting a plurality of splines, one of said splines configured as an axially stationary spline, another of said splines configured as an axially movable spline.

42. The skin defect closing apparatus according to claim 41, wherein each of said splines exhibits an oblique contact surface.

43. The skin defect closing apparatus according to claim 41, wherein said clutch further exhibits a biasing element configured so said axially movable spline is biased toward said axially stationary spline.

44. A skin defect closing apparatus comprising:
a plurality of retaining members, each of said retaining members exhibiting:
at least two legs,
a flange connecting said legs and exhibiting a flange bore located between said legs,
a pivotal base element configured so said base element rotates about a reference position on said retaining member,
a plurality of skin insertion elements, each of said skin insertion elements protruding from a surface of one of said legs; and
a contracting mechanism connecting said retaining members and engaging one of said flange bores, said contracting mechanism configured to approximate said retaining members.

45. The skin defect closing apparatus according to claim 44, wherein each of said retaining members further exhibits a stop for limiting rotational movement of said pivotal base element.

46. The skin defect closing apparatus according to claim 44, wherein said pivotal base element is further configured so said base element rotates from about 0° to about ±20° about the reference position on said retaining member.

* * * * *